(12) United States Patent
Charles

(10) Patent No.: US 11,166,844 B2
(45) Date of Patent: Nov. 9, 2021

(54) RETINAL PATCH GRAFT AND BIOPSY DEVICE

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 56 days.

(21) Appl. No.: 16/829,174

(22) Filed: Mar. 25, 2020

(65) Prior Publication Data
US 2020/0337899 A1 Oct. 29, 2020

Related U.S. Application Data

(60) Provisional application No. 62/838,510, filed on Apr. 25, 2019.

(51) Int. Cl.
*A61F 9/007* (2006.01)
*A61B 10/02* (2006.01)
*A61B 17/3205* (2006.01)

(52) U.S. Cl.
CPC ...... *A61F 9/00736* (2013.01); *A61B 10/0266* (2013.01); *A61B 17/32056* (2013.01)

(58) Field of Classification Search
CPC .. A61F 9/00736; A61F 9/00727; A61F 9/007; A61F 9/00709; A61F 9/00718; A61F 9/00754; A61F 9/00763; A61B 10/0266; A61B 17/32056; A61B 2017/32006; A61B 18/082; A61B 2018/00595; A61B 2018/144; A61B 2018/00601; A61B 2018/1407
See application file for complete search history.

(56) References Cited

U.S. PATENT DOCUMENTS

| 4,732,150 | A | 3/1988 | Keener, Jr. |
| 5,269,787 | A | 12/1993 | Cozean, Jr. et al. |
| 6,066,138 | A | 5/2000 | Sheffer et al. |
| 6,551,326 | B1 | 4/2003 | Van Heugten et al. |
| 8,137,344 | B2 | 3/2012 | Jia et al. |
| 8,157,797 | B2 | 4/2012 | Boukhny et al. |

(Continued)

FOREIGN PATENT DOCUMENTS

| WO | WO2008080149 A1 | 7/2008 |
| WO | WO2018217579 A1 | 11/2018 |

OTHER PUBLICATIONS

Grewal D., Mahmoud TH. Autologous neurosensory retinal free flap for closure of refractory myopic macular holes. JAMA Ophthalmol. Feb. 2016;134(2):229-30 (2 pages).

(Continued)

*Primary Examiner* — George J Ulsh
*Assistant Examiner* — Chima U Igboko

(57) ABSTRACT

Certain aspects of the present disclosure provide an apparatus and method of using a multifunctional device to cut/tab a graft from a donor region of an eye. The apparatus includes a multifunctional device for ophthalmic surgery, having an insertion sleeve comprising an inner surface defining a compartment, a flat wire contained within the compartment folded to form a loop, wherein the flat wire comprises a sharp edge (continuous or tabbed) operable for cutting retinal tissue, and wherein the loop is positioned at a distal end of the insertion sleeve, and a handpiece coupled to the insertion tube and configured to adjust a size of the loop.

8 Claims, 6 Drawing Sheets

(56) References Cited

U.S. PATENT DOCUMENTS

| | | |
|---|---|---|
| 8,162,931 B2 | 4/2012 | Ben-nun |
| 8,814,854 B2 | 8/2014 | Jia |
| 9,125,720 B2 | 9/2015 | Jia |
| 9,241,755 B2 | 1/2016 | Jia |
| 9,351,872 B2 | 5/2016 | Jia |
| 9,861,523 B2 | 1/2018 | Keller |
| 10,070,989 B2 | 9/2018 | Keller |
| 10,206,816 B2 | 2/2019 | Keller |
| 10,278,760 B2 | 5/2019 | Keller |
| 10,285,855 B2 | 5/2019 | Keller |
| 10,363,167 B2 | 7/2019 | Keller |
| 2006/0100617 A1 | 5/2006 | Boukhny |
| 2008/0319463 A1 | 12/2008 | Hickingbotham |
| 2009/0054904 A1* | 2/2009 | Holmen ......... A61B 17/320016 606/107 |
| 2010/0028407 A1* | 2/2010 | Del Priore ............. A61P 17/02 424/443 |
| 2010/0312252 A1 | 12/2010 | Jia et al. |
| 2011/0118734 A1 | 5/2011 | Auld et al. |
| 2014/0194859 A1 | 7/2014 | Ianchulev |
| 2016/0331515 A1* | 11/2016 | Ben Nun ................. A61F 2/148 |
| 2017/0312125 A1 | 11/2017 | Clauson |
| 2018/0036170 A1 | 2/2018 | Ghannoum |
| 2019/0231593 A1 | 8/2019 | Keller |

OTHER PUBLICATIONS

Parolini B, Grewal DS, Pinackatt SJ, Baldi A, Di Salvatore A, Besozzi G, Finzi A, Cardillo D, Mahmoud TH. Combined Autologous Transplantation of Neurosensory Retina, Retinal Pigment Epithelium and Choroid Free Grafts. Retina. Sep. 2018;38 Suppl 1:S12-S22. doi: 10.1097/IAE.0000000000001914 (19 pages).

Thomas AS, Mahmoud TH. Subretinal Transplantation of an Autologous Retinal Free Flap for Chronic Retinal Detachment with Proliferative Vitreoretinopathy With and Without Macular Hole. Retina. Sep. 2018;38 Suppl 1:S121-S124 (4 pages).

Grewal DS, Charles S, Parolini B, Kadonosono K, Mahmoud TH. Autologous Retinal Transplant for Refractory Macular Holes: Multicenter International Collaborative Study Group. Ophthalmology. Jan. 31, 2019. pii: S0161-6420(18) 32595-8. doi: 10.1016/j.ophtha.2019.01.027. [Epub ahead of print] (10 pages).

* cited by examiner

RETINAL PATCH GRAFT AND BIOPSY DEVICE

PRIORITY CLAIM

This application claims the benefit of priority of U.S. Provisional Patent Application Ser. No. 62/838,510 titled "Retinal Patch Graft and Biopsy Device", filed on Apr. 25, 2019, whose inventor is Dr. Steven T. Charles, which is hereby incorporated by reference in its entirety as though fully and completely set forth herein.

TECHNICAL FIELD

The present invention relates in general to surgical instruments and surgical techniques for cell and tissue isolation. More particularly, the present invention is directed to a multifunctional surgical device for precise measuring of a macular hole as well as cutting/tabbing and/or coagulation of retinal tissue for macular hole grafting.

BACKGROUND

The rays of light entering the eye and bearing the pattern of the environment being looked upon pass through the cornea, the aqueous humor, the pupil, the lens, and the vitreous humor, then fall upon the retina. The retina is the light sensitive film lining the back two-thirds of the eye. If these parts of the eye are normal and the lens is properly adjusted, the image will be focused upon the retina. This condition results in clear vision.

At the back of the eye or, more specifically, the back part of the retina is the macula. The macula is a small region of the retina (about 3 millimeters (mm) by 5 mm) adjacent to the optic nerve. Vision in which the image of the environment looked upon falls upon the macula is the sharpest vision and is called macular vision or central vision, as opposed to gross, peripheral vision.

Most of the eye's interior is filled with vitreous, a gel-like substance that takes up about four-fifths of the eye's volume. The vitreous contains millions of fine fibers that are attached to the surface of the retina. Aging can cause the vitreous to shrink and pull away from the retinal surface. In many cases, when the vitreous pulls away, the retina can tear and create a macular hole, causing blurred and distorted central vision.

Currently, surgical solutions for repairing macular holes include retinal patch grafting, whereby a portion of healthy retina is removed from a donor region of the eye and grafted in the macular hole. However, these solutions rely on imprecise visual estimation to determine macular hole and graft size. Moreover, these solutions apply bipolar cautery and laser retinopexy in a circular fashion around the donor region, followed by vertical scissors to cut the graft, followed again by positioning the graft in the macular hole with forceps. As such, contemporary solutions for repairing macular holes utilize imprecise measuring and require a broad array of tools to complete the grafting.

BRIEF SUMMARY

The present disclosure relates to a multifunctional surgical device for precise measuring of a macular hole as well as cutting/tabbing and/or coagulation of retinal tissue for macular hole grafting.

Certain embodiments provide a multifunctional device for ophthalmic surgery. The multifunctional device includes an insertion sleeve comprising an inner surface defining a compartment, a flat wire contained within the compartment folded to form a loop, wherein the flat wire comprises a sharp edge operable for cutting retinal tissue, and wherein the loop is positioned at a distal end of the insertion sleeve, and a handpiece coupled to the insertion sleeve and configured to adjust a size of the loop.

Also, certain embodiments provide a method of using the multifunctional device to cut (e.g., through a sharp edge or application of heat) a graft from a donor region of an eye. The method includes inserting a distal end of an insertion sleeve into the eye via a cannula, wherein the insertion sleeve comprises a loop formed by a flat wire, and wherein the loop is configured to extend out from the distal end. The method also includes positioning the distal end adjacent to a hole in a macular region of the eye, and adjusting a diameter of the loop to measure the macular hole. The method further includes positioning the distal end adjacent to the donor region of the eye, the donor region being outside of the macular region, and positioning the loop having the adjusted diameter in contact with the donor region. The method further includes applying pressure to the donor region via the loop to cut (e.g., through a sharp edge or through application of heat through the loop) the graft from the donor region.

Also, certain embodiments provide a method of using the multifunctional device to mechanically cut/tab a graft from a donor region of an eye. The method includes inserting a distal end of an insertion sleeve into the eye via a cannula, wherein the insertion sleeve comprises a loop formed by a flat wire, and wherein the loop is configured to extend out from the distal end. The method also includes positioning the distal end adjacent to a hole in a macular region of the eye, and adjusting a diameter of the loop to measure the macular hole. The method further includes positioning the distal end adjacent to the donor region of the eye, the donor region being outside of the macular region, and positioning the loop having the adjusted diameter in contact with the donor region. The method further includes applying pressure to the donor region via the loop to cut the graft from the donor region (possibly with one or more tabs still linking the graft to the donor region).

If the graft was tabbed, the forceps may be used to grab and separate the graft from the surrounding tissue in the donor region. In some embodiments, a medium term perfluorocarbon liquid (PFO) may be used to oxygenate the graft instead of direct PFO-oil exchange. PFO carries more oxygen than hemoglobin while silicone oil has low oxygen extraction ratio.

Further, certain embodiments provide a kit for use in performing ophthalmic surgery. The kit includes an insertion sleeve comprising an inner surface defining a compartment, a flat wire contained within the compartment folded to form a loop, wherein the flat wire comprises a sharp edge operable for cutting retinal tissue, and wherein the loop is positioned at a distal end of the insertion sleeve, and a handpiece coupled to the insertion sleeve and configured to adjust a size of the loop.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide a multifunctional surgical device configured to provide a user with solutions for precisely measuring a macular hole and graft size. Moreover, the solutions described herein reduce the number of surgical instruments required to implement macular grafting by allowing the user to utilize a single device for both measurement procedures and cutting procedures.

Figure 1:
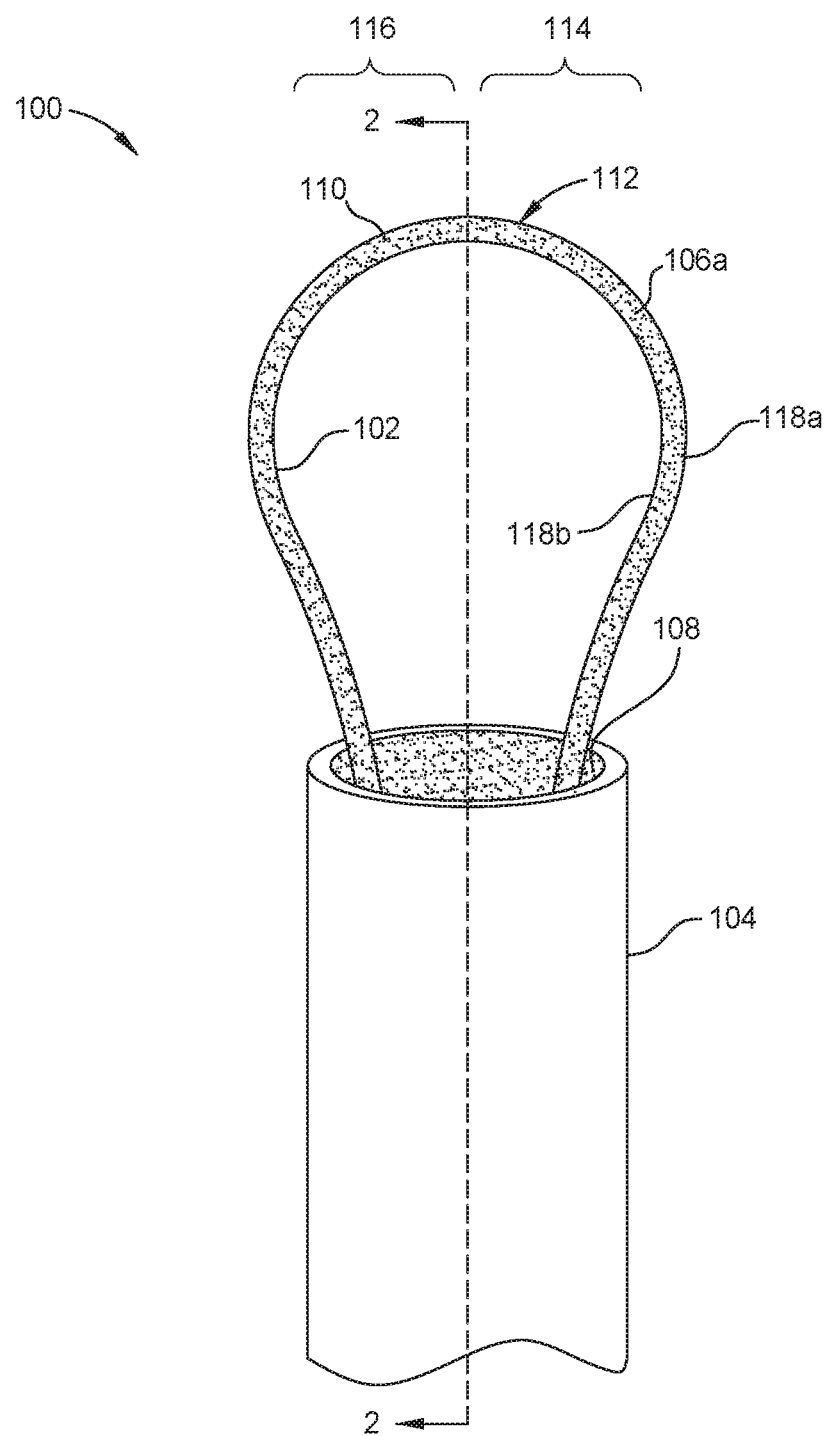
FIG. 1 illustrates a perspective view of a distal end of a multifunctional surgical device configured for measuring, cutting/tabbing and/or coagulation during a retina patch graft procedure, according to some embodiments of the present disclosure.

FIG. 1 illustrates a perspective view of a distal end of a multifunctional surgical device 100 configured for measuring a macular hole, as well as cutting/tabbing (impartial cutting) and/or coagulation and cutting of a part of a retina for grafting over the macular hole. Note that herein a distal end of surgical device 100 refers to the end that is closer to a patient's body. On the other hand, the proximal end of surgical device 100 refers to the end that is facing away from the patient's body. Here, the distal end includes a substantially circular, flexible loop 112 of flat wire 102 that can be extended and retracted from an insertion sleeve 104 such that the size or diameter of the loop 112 can be adjusted. The loop 112 is formed by folding the flat wire 102 such that a first length 114 and a second length 116 of the flat wire 102 (both extending in opposite directions from an apex of the loop 112) are housed within the insertion sleeve 104. It should be noted that the terms "first length" and "second length" are meant to be descriptive of certain portions of the flat wire 102 shown in the illustrations; hence, the terms are not meant to be limiting or indicative of upper and/or lower bounds of the flat wire 102 or loop 112 lengths.

In one example, first length 114 can be extended in a distal direction from the insertion sleeve 104, while the second length 116 remains in a static position. In this example, the diameter of the loop 112 will expand out from the insertion sleeve 104. In another example, the first length 114 can be retracted into the insertion sleeve 104, while the second length 116 remains in a static position. In this example, the diameter of the loop 112 will be reduced and the loop 112 will be retracted into the insertion sleeve 104. In some embodiments, the diameter of the loop 112 may be adjusted within a range of 0.25-6 mm (millimeters). As further described in relation to FIG. 3A, a surgeon is able to measure the size of a macular hole in the retina by adjusting the size of loop 112 in relation to the hole.

The flat wire 102 may include multiple edges defining the wire's profile. In one embodiment, the flat wire 102 includes two edges: an outer edge 118a and an inner edge 118b formed by a convergence to two flat surfaces (a first flat surface 106a is shown in FIG. 1). The outer edge 118a is sharp and can be utilized for cutting (with or without tabs) and/or applying an electrical current to a portion of retinal tissue to create a graft, while the inner edge 118b is rounded to improve adhesion of an insulating material described in more detail below.

In some embodiments, the flat wire 102 may be formed from a nickel titanium alloy material, such as Nitinol, which may exhibit superelastic or pseudoelastic and shape memory characteristics. Because Nitinol is characterized by superelasticity, it is able to withstand a significant amount of deformation when a load is applied (e.g., when the flat wire 102 is folded and/or the loop is compressed within the insertion sleeve 104) and return to its original shape when the load is removed. Further, Nitinol is resistive, and thus, the flat wire 102 can optionally be heated with an electrical current. As described below, heat caused by an electrical current or potential is used may be used to cause coagulation of bleeding vessels either on the retinal surface or beneath pre-retinal membranes when the flat wire 102 is used to cut tissue (e.g., retinal tissue). It should be noted that in alternative embodiments, the flat wire 102 may be formed of other materials having resistive and/or superelastic characteristics instead of Nitinol. It should also be noted that the flat wire may cut tab(s) in the retina tissue without heat and without cutting all the way through the tissue to prevent the graft from floating away. In some embodiments, most of the loop may be cut with the exception of a single tab. In some embodiments, uncut tabs may be spaced around the loop (as determined by the cutting surface on the flat wire).

In some embodiments, the insertion sleeve 104 is a cylindrical tube configured to be inserted into an eye via a cannula 304 (see FIGS. 3A and 3B) during a surgical procedure. The insertion sleeve 104 is formed from a surgical stainless steel or a thermoplastic material. Although surgical stainless steel has low thermal conductivity relative to other metals and metal alloys, an electrically insulating material 108 may optionally be disposed over an inside surface of the insertion sleeve 104 to prevent shorting or transfer of an electrical current from the flat wire 102 to the insertion sleeve 104 (i.e., so electrical current travels around the flat wire 102 loop). Electrically insulating material 110 may also optionally be disposed on a flat surface and/or the inner edge 118b of flat wire 102 to prevent arching of an electrical current between the first length 114 and the second length 116 of the flat wire 102, and to reduce or eliminate electrochemical reaction (e.g., a steam "explosion" in vitreous material caused by rapid heating of the flat wire 102). For example, the insulating material 110 may be utilized to minimize the surface area of the flat wire 102 loop having direct contact with matter (e.g., vitreous body) or surfaces (e.g., retinal tissues) inside of the eye. Accordingly, heat-affected regions of the flat wire 102 having direct contact with portions of the eye can be reduced to prevent collateral thermal damage to other regions of the eye. Insulating material (108 and/or 110) may include a bio-compatible and temperature resistant material, such as a polyamide. In some embodiments, insulating material (108 and/or 110) is flexible to accommodate flexibility in the flat wire 102.

In some embodiments, the insertion sleeve 104, insulating material (108 and 110), and flat wire 102 are a disposable unit removably attached to a handpiece (see handpiece 302 of FIGS. 3A and 3B) or other apparatus. In some embodiments, insertion sleeve 104 may be permanently coupled to the handpiece.

Figure 2:
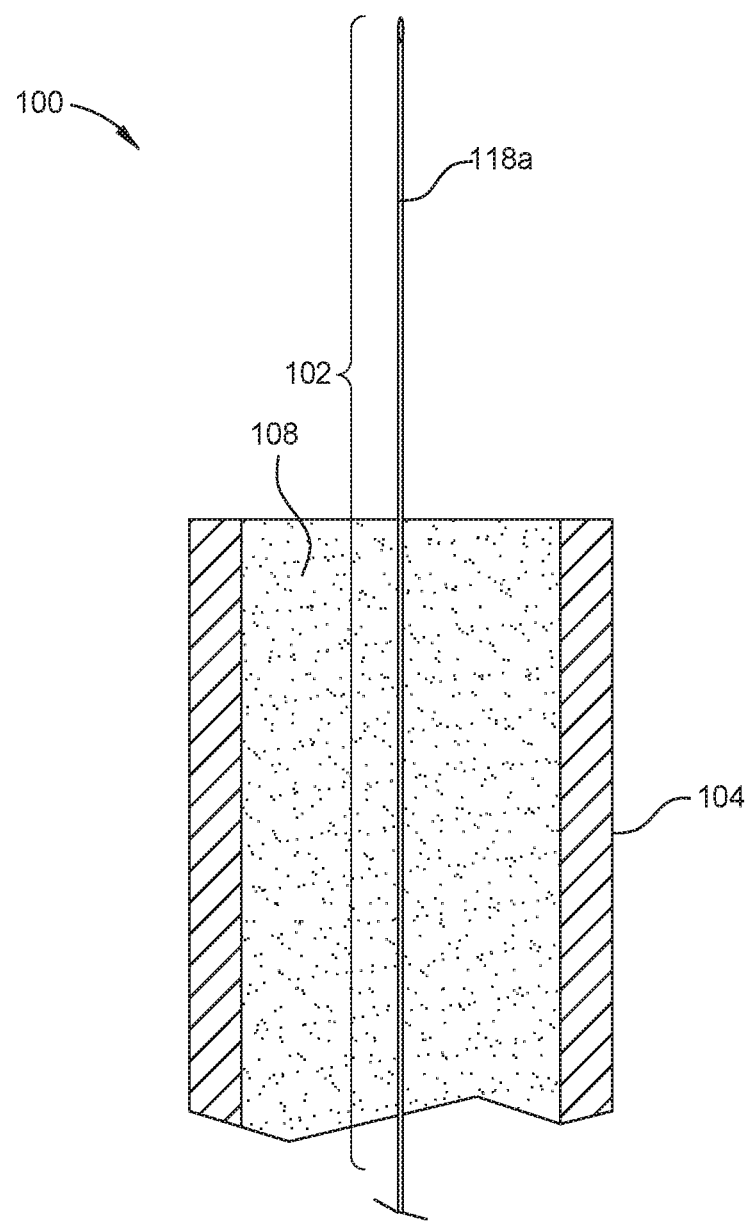
FIG. 2 illustrates a cross-sectional view of the distal end shown in FIG. 1.

FIG. 2 illustrates a cross-sectional view of the distal end of the surgical device of FIG. 1, showing the outer edge 118a of the flat wire 102. It should be noted that the flat wire in FIGS. 1 and 2 is oriented to illustrate pertinent aspects and to enhance clarity of the disclosure. As such, this disclosure is not necessarily limited to the orientation illustrated in FIGS. 1 and 2, and may include additional orientations (e.g., an orientation where the flat wire is rotated 90 degrees such that outer edge 118a and the inner edge 118b form a single loop instead of an inside loop and an outside loop).

Figure 3A:
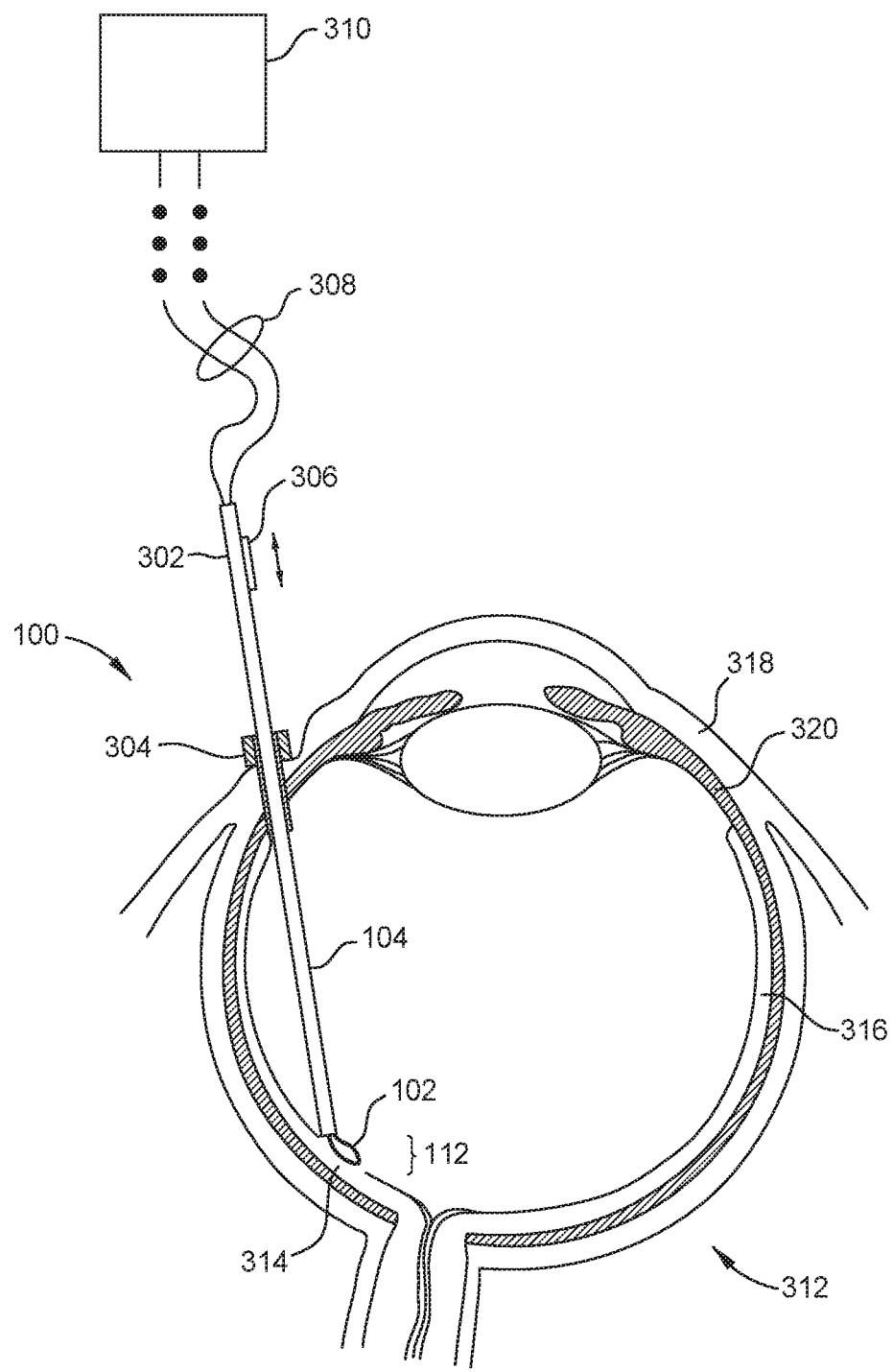
FIG. 3A illustrates a side view of the multifunctional surgical device measuring a macular hole in the retina of an eye, according to some embodiments of the present disclosure.

FIG. 3A illustrates a side view of a multifunctional surgical device 100 measuring a macular hole 314 in the retina 316 of an eye 312. As shown, the surgical device 100 includes a handpiece 302, an insertion sleeve 104, a linear slider 306 element, and a flat wire 102. The handpiece 302 includes a housing configured to be held for operation of the surgical device 100. The flat wire 102 includes a first length and a second length folded to form a loop, and is contained within the insertion sleeve. In some embodiments, handpiece 302, insertion sleeve 104, slider 306, optional insulating material (108 and 110), and flat wire 102 are a kit that collectively form a disposable unit or kit.

Each of the first length and the second length of the flat wire 102 may be electrically coupled to one of the two electrical connectors 308. The electrical connectors 308 provide an interface between the surgical device 100 and the power source 310. The power source 310 is configured to electrically energize the flat wire 102 so that an electrical current and/or voltage may be passed through the loop 112 for cauterizing. The slider 306 provides the user with a means for extending and retracting (e.g., adjusting the size of) the loop 112 at the distal end of the insertion sleeve 104, as described in more detail below. In some configurations, the slider 306 may include any suitable means (e.g., lever, actuating motor with push button, etc.) for extending and retracting the loop 112.

As shown in FIG. 3A, the insertion sleeve 104 is inserted into the eye 312 via a cannula 304. The insertion sleeve 104 may have a length between 10-50 mm in length. The cannula 304 is configured to allow the user to insert various surgical devices into the eye 312 without causing trauma to the surrounding tissue (e.g., sclera 318, ciliary 320, etc.). In some embodiments, the cannula 304 is inserted into the eye 312 after making a small incision in the sclera 318 and ciliary body 320. Cannula 304 may range from 18 to 27 gauge having a length of 4-8 mm. Once the insertion sleeve 104 is inserted into the eye 312 via cannula 304, a user can move the handpiece 302 to vary the position and depth of the insertion sleeve 104 within the eye 312. In this example, the tip of the insertion sleeve 104 is positioned adjacent to the macular hole 314 in the retina 316 so that the loop 112 can be adjusted to allow the user to gauge the size of the macular hole 314 and determine a loop 112 diameter suitable for cutting/tabbing a graft of retinal tissue from a donor site 322. In some embodiments, graft donor sites may be selected near the macula to achieve adaptive synaptogenesis rather than peripheral sites (however, in some embodiments, peripheral sites may be used).

Figure 3B:
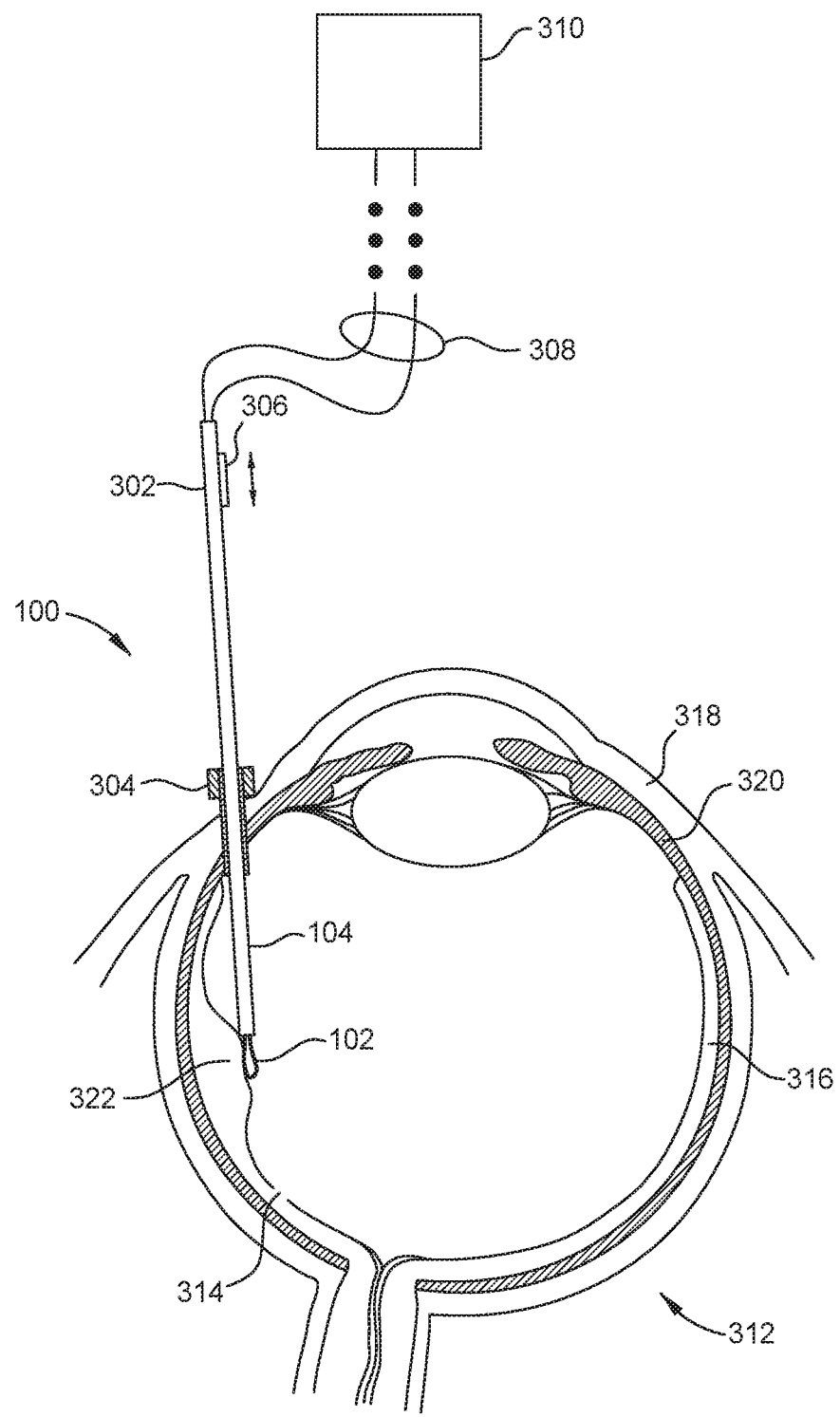
FIG. 3B illustrates a side view of the multifunctional surgical device cutting a graft from a donor site in the eye, according to some embodiments of the present disclosure.

FIG. 3B illustrates a side view of the multifunctional surgical device 100 cutting/tabbing a graft from the donor site 322 of the retina 316 for repairing the macular hole 314. Note that the user may retain the determined loop 112 diameter to ensure that the graft cut/tabbed from the donor site 322 is appropriately sized. For example, a locking mechanism may be used in handpiece 302 to lock the size of loop 112.

Figure 4A:
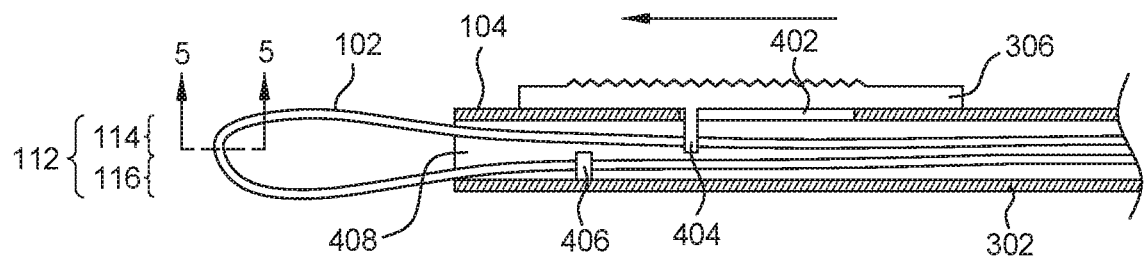
FIG. 4A illustrates a cross-sectional view of a handpiece and an insertion sleeve with a slider in a deployed position, according to some embodiments of the present disclosure.

FIG. 4A illustrates a cross-sectional view of the handpiece 302 and insertion sleeve 104 with slider 306 in a fully extended position. In this example, the slider 306 is configured for linear movement across an outer surface of the handpiece 302. The slider 306 includes a first segment 404 that extends into a compartment 408 of the insertion sleeve 104 via a slot 402 in the insertion sleeve 104. The first segment 404 is coupled to a portion of a first length 114 of the flat wire 102, such that movement of the slider 306 corresponds to a movement of the first length 114 within the insertion sleeve.

The compartment 408 of the insertion sleeve 104 includes a second segment 406 coupled to a portion of a second length 116 of the flat wire 102 within the compartment 408. As such, movement of the slider 306 to the fully extended position (i.e., when the user pushes the slider 306 toward the distal end of the insertion sleeve 104) will extend the loop 112 from the tip of the insertion sleeve 104 and expand the diameter of the loop 112. In some configurations, the slider 306 is coupled to both the first length 114 and the second length 116 of flat wire 102, instead of the second length 116 being coupled to the compartment 408. In such a configuration, the diameter of the loop can be adjusted with relatively less movement of the slider 306.

Figure 4B:
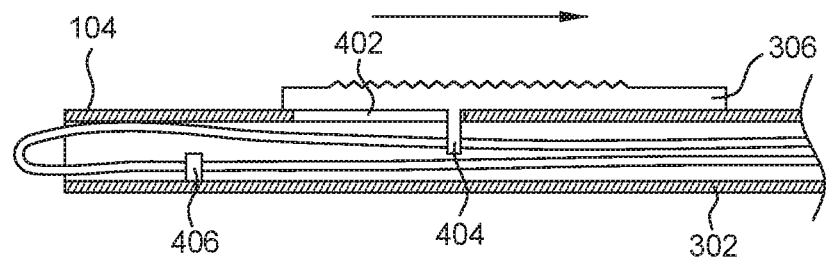
FIG. 4B illustrates a cross-sectional view of the handpiece and insertion sleeve with slider in a non-deployed position, according to some embodiments of the present disclosure.

FIG. 4B illustrates a cross-sectional view of the handpiece 302 and insertion sleeve 104 with slider 306 in a fully retracted, non-deployed position. When the slider 306 is pulled back along the slot 402 and away from the tip of the insertion sleeve 104, the exposed length of the flat wire 102 may be pulled back into the compartment 408, thereby reducing the diameter of the loop 112.

While the examples illustrated in FIGS. 4A and 4B illustrate the slider 306 in either of a fully extended (i.e., deployed) or fully retracted position (i.e., non-deployed), it will be apparent to those skilled in the art that the loop 112 can be extended and retracted in varying degrees within the slot 402 utilizing the slider 306.

Figure 5:
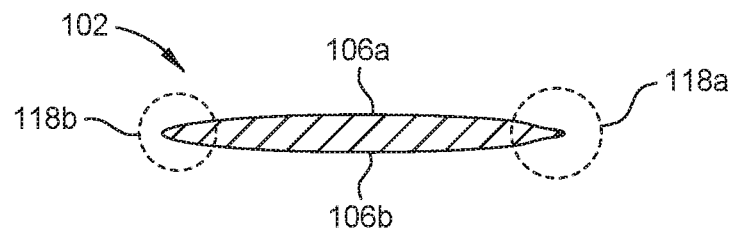
FIG. 5 illustrates a cross-sectional view of a flat wire identified by a section line in FIG. 4A.

FIG. 5 illustrates a cross-sectional view of the flat wire 102 identified by a section line at the flat wire 102 loop in FIG. 4A. The flat wire 102 includes a first flat surface 106a and a second flat surface 106b. Each of the flat surfaces (106a and 106b) tapers out to an inner edge 118b and an outer edge 118a on opposite sides of the flat wire 102. In some configurations, the inner edge 118b is rounded or blunt relative to the outer edge 118a which includes a sharp edge configured for cutting/tabbing. In some configurations, either or both the inner edge 118b and the outer edge 118a may include a sharp edge. In some embodiments, the sharp edge may be continuous all the way around the loop or may have one or more tab-sized portions to leave portions of the graft circumference uncut.

In some embodiments, a portion of the flat surfaces (106a and 106b) and the rounded inner edge 118b may include an insulating material 110 disposed thereon, leaving the sharp edge of the outer edge 118a without insulating material 110.

The flat wire 102 may vary in dimension. In one example, the flat wire 102 has a width of 50 micro-meters (μm) between the inner edge 118b and the outer edge 118a. In some configurations, the width is within a range of 25 μm to 100 μm.

Figure 6:
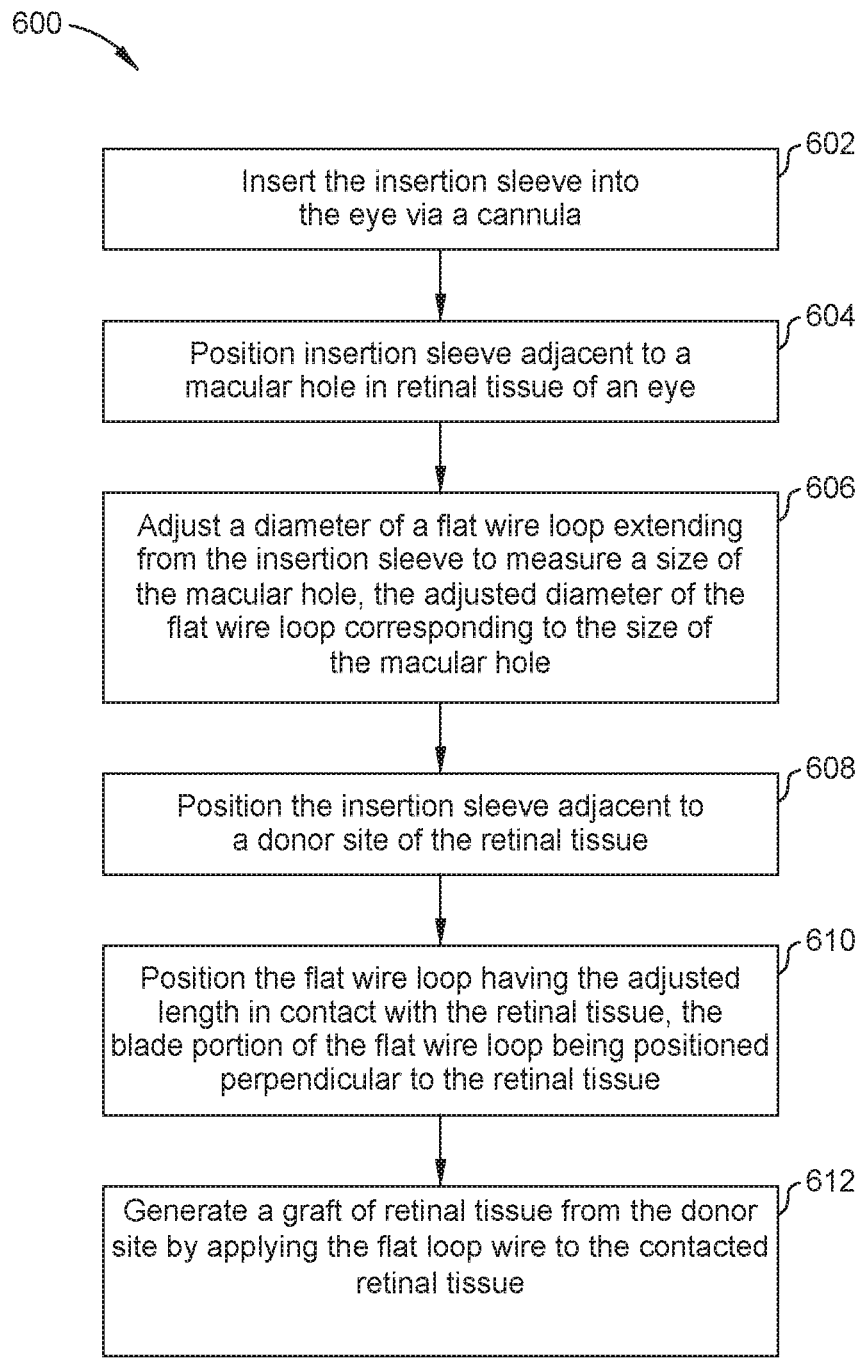
FIG. 6 is a flow chart illustrating an example method for utilizing the multifunctional surgical device, according to some embodiments of the present disclosure.

FIG. 6 is a flow chart illustrating an example method 600 for utilizing the foregoing multifunctional surgical device 100 according to some embodiments. Various elements provided by the example method 600 may be omitted, additional elements may be added, and/or various elements may be performed in a different order than shown and described below.

Initially, an incision is made in an eye 312, and a cannula 304 is positioned within the incision. At 602, a user grasps the handpiece 302 and inserts the insertion sleeve 104 into the eye 312 via the cannula 304. In some embodiments, the user utilizes a partially exposed loop 112 (as shown in FIG. 4B) to guide the insertion sleeve 104 into the cannula 304. For example, the user may introduce the partially exposed loop 112 into the cannula 304 to aid insertion of the insertion sleeve 104 into the cannula 304.

At 604, the insertion sleeve 104 is inserted into the eye 312 via the cannula 304, and the insertion sleeve 104 is positioned adjacent to a macular hole 314 in the retinal tissue 316.

At 606, the user adjusts the size of loop 112 to match the size of macular hole 314. For example, the user extends the flat wire 102 utilizing the slider 306 to move the loop 112 out of the insertion sleeve 104 and expand the diameter of the loop 112. The size of the loop 112 is adjusted to allow the user to gauge the size of the macular hole 314 relative to the loop 112, and to determine an appropriate loop 112 size for grafting. For example, the user may position the loop 112 over the macular hole 314 and adjust the loop 112 such that it behaves like an internal caliper for measuring the macular hole 314. The user can retain the determined loop 112 size for cutting a graft that will adequately cover the macular hole 314.

At 608, the user re-positions the insertion sleeve 104 adjacent to a donor region or site 322 of the retinal tissue 316 in the eye 312. In some embodiments, graft donor sites may be selected near the macula to achieve adaptive synaptogenesis rather than peripheral sites (however, in some embodiments, peripheral sites may be used).

At 610, the user positions the loop 112 such that the outer edge 118a (i.e., a sharp edge) of the flat wire 102 is in contact with the retinal tissue 316 of the donor site 322 (i.e., the flat wire 102 is oriented perpendicular to the retinal tissue 316).

At 612, the user may generate a graft of the retinal tissue 316 from the donor site 322 by mechanically cutting/tabbing the graft. In some embodiments, the graft may be formed by electrically energizing the flat wire 102 via the power source. For example, resistance in the flat wire 102 will cause the loop 112 to heat when electrically energized. In this way, any portion of the loop 112 in contact with the retinal tissue 316 will define a weakened boundary for detachment of the retinal tissue 316 for grafting. In this example, the heat at the outer edge 118a of the flat wire 102 will result in coagulation and weakening of the contacted portion of the retinal tissue 316. Other methods of generating a graft are also contemplated. For example, in some embodiments, the graft may originate from an external source.

In some embodiments, the flat wire 102 may be electrically energized via a short pulse (e.g., 20 milliseconds) of electrical current, or a series of pulses (e.g., 1 millisecond each). In some embodiments, pulsed radio-frequency power is used to reduce collateral thermal damage to the donor site 322 and avoid electrochemical reaction (e.g., a steam "explosion" in vitreous material caused by rapid heating of the flat wire 102), or arching between opposing sides of the flat wire 102. The frequency, waveform, voltage, pulse width, and duration of the radio-frequency power may be configured to attain a continuous through-cut on retina tissue 316 while reducing collateral damage. Those skilled in the art will appreciate that the power settings (e.g., voltage, current, pulse width, number of pulses, etc.) may be established for a particular flat wire 102 configuration (e.g., gauge, length, material, etc. of the flat wire 102) so that a continuous cut may be attained while minimizing damage to tissue surrounding the portion being removed for grafting.

The user then cuts the weakened contact portion of the retinal tissue 316 with the outer edge 118a of the flat wire 102 by adjusting the position of the insertion sleeve 104 to apply downward pressure against the contacted retinal tissue 316. Because the loop is extended out from the insertion sleeve 104, the pressure may be applied at such an angle that the full length of the loop 112 comes into contact with the retinal tissue, allowing for a continuous and uniform cut if the blade is continuous or a tabbed cut if the blade has one or more tabs. In some embodiments, the entire blade may leave a weakened tab around the entire circumference of the graft. The pressure cuts the retinal tissue 316 around the contacted donor site 322 in a trephine-like fashion with the outer edge 118a of the flat wire 102, allowing removal of the graft. Note that, in some embodiments, a user may cut/tab a graft by pressing the outer edge 118a onto donor site 322 to cut/tab a graft. Accordingly the techniques described above in relation to applying downward pressure against the contacted retinal tissue 316 to cut/tab a graft are applicable regardless of whether or not the contacted portion of the retinal tissue 316 is previously coagulated and weakened as a result of electrically energizing the flat wire 102.

Once the retinal tissue is cut/tabbed, the insertion sleeve 104 may be removed from the eye 312. In some embodiments, the cut portion of the retinal tissue may be removed from the donor site 322 and placed over the macular hole 314 using a surgical instrument such as forceps. If the graft was tabbed, the forceps may be used to grab and separate the graft from the surrounding tissue. In some embodiments, a medium term perfluorocarbon liquid (PFO) may be used to oxygenate the graft instead of direct PFO-oil exchange. PFO carries more oxygen than hemoglobin while silicone oil has low oxygen extraction ratio.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A method of using a multifunctional device to cut a graft from a donor region of an eye, the method comprising:
   inserting a distal end of an insertion sleeve into the eye via a cannula, wherein the insertion sleeve comprises a loop formed by a flat wire, and wherein the loop is configured to extend out from the distal end;
   positioning the distal end adjacent to a hole in a macular region of the eye;
   adjusting a diameter of the loop to measure the macular hole;

positioning the distal end adjacent to the donor region of the eye, the donor region being outside of the macular region;

positioning the loop having the adjusted diameter in contact with the donor region; and applying pressure to the donor region via the loop to cut the graft from the donor region.

2. The method of claim 1, wherein adjusting the diameter of the loop further comprises adjusting a slider element attached to a portion of the flat wire.

3. The method of claim 1, wherein the flat wire comprises two tapering surfaces configured to form a sharp edge.

4. The method of claim 3, wherein the two tapering surfaces are substantially flat and on opposite sides of the flat wire, and wherein each of the two tapering surfaces comprise an electrically insulating material disposed thereon.

5. The method of claim 1, wherein the flat wire comprises a material having superelastic characteristics.

6. The method of claim 1, further comprising:

electrically energizing the loop via a power source to cauterize the donor region.

7. The method of claim 6, wherein the power source is configured to electrically energize the loop via a pulse of electrical current.

8. The method of claim 7, wherein the insertion sleeve further comprises an inner surface defining a compartment within the insertion sleeve, and wherein the inner surface comprises an electrically insulating material disposed thereon.

* * * * *